(12) United States Patent
Aerts et al.

(10) Patent No.: US 8,366,934 B2
(45) Date of Patent: Feb. 5, 2013

(54) METHOD FOR THE ELUTION OF 18F FLUORIDE TRAPPED ON AN ANION-EXCHANGE PHASE IN A FORM SUITABLE FOR EFFICIENT RADIOLABELING WITHOUT ANY EVAPORATION STEP

(75) Inventors: Joel Aerts, Durbuy (BE); Christian LeMaire, Alleur (BE); Steve Lignon, Juprelle (BE); André Luxen, Ocquier (BE); Jean-Luc Morelle, Liege (BE); Gauthier Philippart, Grand-Rechain (BE); Samuel Voccia, Liege (BE)

(73) Assignees: Trasis S.A., Liege (BE); Universite de liege, Liege (BE)

( * ) Notice: Subject to any disclaimer, the term of this patent is extended or adjusted under 35 U.S.C. 154(b) by 435 days.

(21) Appl. No.: 12/528,284

(22) PCT Filed: Feb. 19, 2008

(86) PCT No.: PCT/BE2008/000012
§ 371 (c)(1),
(2), (4) Date: Sep. 28, 2010

(87) PCT Pub. No.: WO2008/101305
PCT Pub. Date: Aug. 28, 2008

(65) Prior Publication Data
US 2011/0006011 A1 Jan. 13, 2011

Related U.S. Application Data

(60) Provisional application No. 60/902,428, filed on Feb. 21, 2007.

(30) Foreign Application Priority Data

Jun. 11, 2007 (EP) .................................. 07447036

(51) Int. Cl.
*B01D 15/08* (2006.01)
(52) U.S. Cl. ..... 210/635; 210/656; 210/682; 210/198.2; 424/1.89
(58) Field of Classification Search .................. 210/635, 210/656, 659, 682, 198.2; 424/1.89
See application file for complete search history.

(56) References Cited

U.S. PATENT DOCUMENTS

| 4,606,908 A | 8/1986 | Bassingthwaighte et al. |
| 5,425,063 A | 6/1995 | Ferrieri et al. |
| 8,206,571 B2 * | 6/2012 | Clarke ........................... 205/350 |

(Continued)

FOREIGN PATENT DOCUMENTS

| CN | 1 887 828 | 1/2007 |
| EP | 0 588 480 A1 | 8/1993 |
| EP | 0 798 307 A1 | 10/1997 |
| JP | 04-077699 | 3/1992 |
| WO | WO 2006/065038 A1 | 6/2006 |

OTHER PUBLICATIONS

Kim et al., "A new class of SN2 reactions catalyzed by protic solvents: Facile fluorination for isotopic labeling of diagnostic molecules," *J. Am. Chem. Soc.* (2006) 128: 16394-16397.

*Primary Examiner* — Ernest G Therkorn
(74) *Attorney, Agent, or Firm* — Merchant & Gould P.C.

(57) ABSTRACT

A method extracts out of an aqueous solution, concentrate and/or reformulate [18F] fluorides without any evaporation step. The eluting solution is a low water content, preferably <3% water, organic solution containing at least:
  a first compound (A) which is a tertiary alcohol-function bearing molecule,
  a second compound (B) which is a phase transfer agent suitable for radiolabeling and which is necessary to the anion exchange process.

28 Claims, 1 Drawing Sheet

(A)

(B)

U.S. PATENT DOCUMENTS

| | | | |
|---|---|---|---|
| 8,206,593 B2 * | 6/2012 | Lee et al. | 210/640 |
| 2007/0071671 A1 * | 3/2007 | Hirano | 424/1.11 |
| 2008/0019906 A1 | 1/2008 | DiMagno et al. | |
| 2008/0281090 A1 * | 11/2008 | Lee et al. | 536/122 |
| 2009/0242421 A1 * | 10/2009 | Clarke | 205/350 |
| 2009/0277804 A1 * | 11/2009 | Clarke | 205/742 |
| 2010/0196254 A1 * | 8/2010 | Lemaire et al. | 423/501 |
| 2011/0006011 A1 * | 1/2011 | Aerts et al. | 210/682 |

* cited by examiner

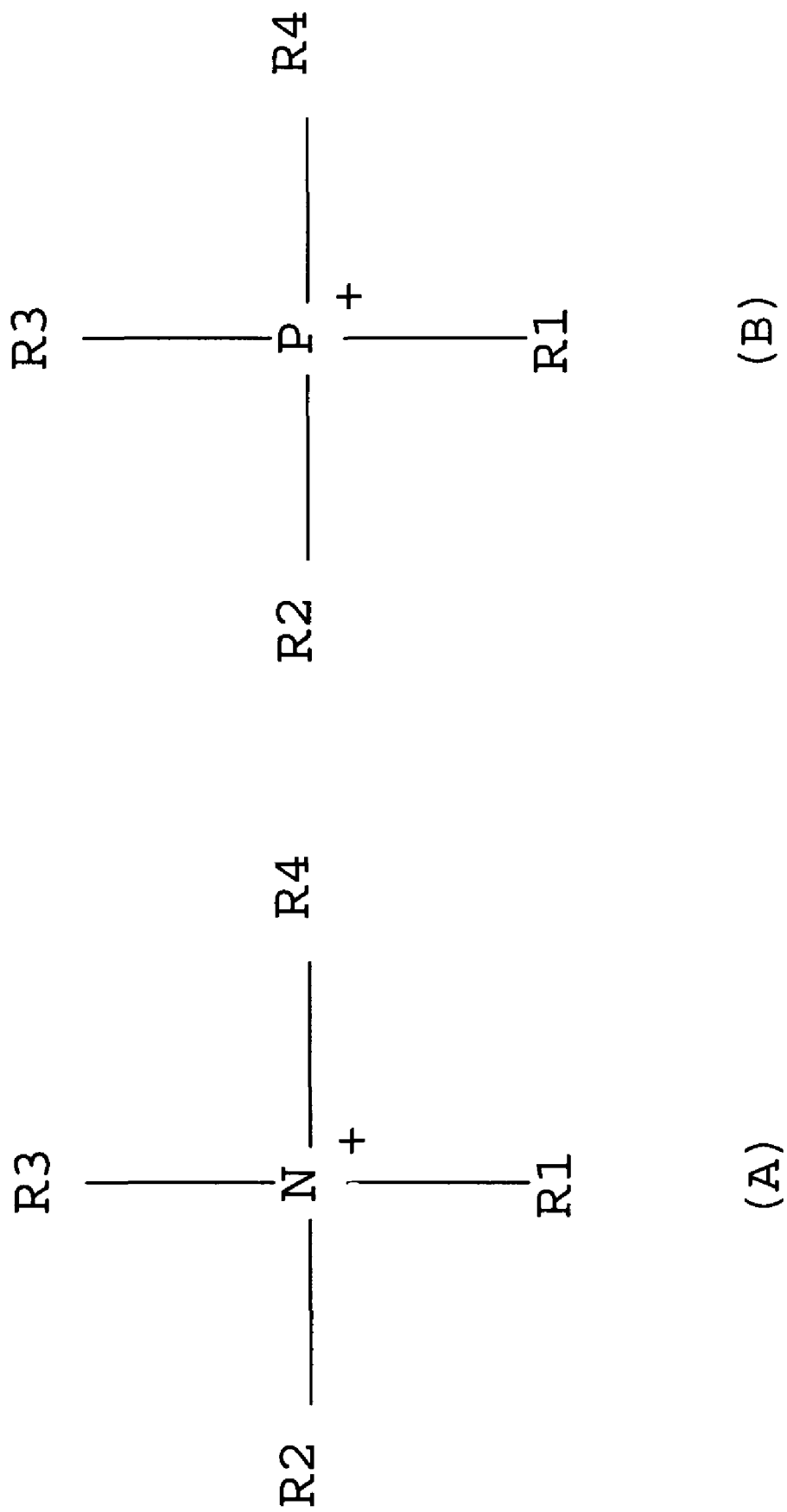

METHOD FOR THE ELUTION OF 18F FLUORIDE TRAPPED ON AN ANION-EXCHANGE PHASE IN A FORM SUITABLE FOR EFFICIENT RADIOLABELING WITHOUT ANY EVAPORATION STEP

This application is a National Stage Application under 35 USC 371 of PCT/BE2008/000012, filed Feb. 19, 2008, which claims benefit of Serial No. 07447036.0, filed Jun. 11, 2007 in the EPO, and also of Ser. No. 60/902,428, filed Feb. 21, 2007 in the United States and which application(s) are incorporated herein by reference. To the extent appropriate, a claim of priority is made to each of the above disclosed applications.

TECHNICAL FIELD

The present invention relates to methods for the elution of [18F] fluoride activity from an aqueous solution and trapped on an anion-exchange resin or phase in a form suitable for efficient radiolabeling without an evaporation step.

BACKGROUND ART

[18F] fluoride is produced by irradiation of water, containing $H_2^{18}O$, with protons resulting in the reaction $^{18}O(p,n)^{18}F$. Only a minor fraction of the [18O] is converted. The [18F] isotope is then separated from the water and processed for production of a radiopharmaceutical agent.

In the current practice, fluoride recovery is based on the use of an anion-exchange resin. The recovery is carried out in two steps, extraction and elution: first the anions (not only fluoride) are separated from the enriched [18O] water and trapped on the said resin. The anions, including [18F] fluoride, are then eluted into a mixture containing water, organic solvents, a phase transfer agent or activating agent or phase transfer catalyst, such as for example the complex potassium carbonate-Kryptofix 222 ($K_2CO_3$—K222) or a tetrabutyl-ammonium salt. The [18F] fluoride radiochemical recovery yield is very effective, usually exceeding 99%.

The most usual labeling method, known as nucleophilic substitution, requires anhydrous or very low water content solutions. Thus, an evaporation step (or drying step) is still necessary after recovery to remove the excess water. It usually consists in multiple azeotropic evaporations of acetonitrile or of low boiling temperature organic solvent. Such evaporations require several minutes.

The current trend in the automation of the preparation of radiopharmaceuticals for medical imaging is to develop "Lab-on-chip" devices. The aforementioned evaporation step is very difficult to implement within such a "Lab-on-chip" device.

AIMS OF THE INVENTION

The current invention aims at avoiding the need for any evaporation at the stage of the elution on the anion-exchange resin or phase.

Further the invention aim to reduce the preparation duration, which results in an increase of the overall yield.

A still further aim of the invention is to simplify the automated equipment used for the synthesis of a radiotracer.

Further the invention aims at making the method suitable for implementation into macro- and microsystems, in particular automated "Lab-on-chip" systems.

SHORT DESCRIPTION OF THE DRAWINGS

FIG. 1A and FIG. 1B schematically represent the ammonium and the phosphonium salt molecules respectively used in the elution solution.

R1, R2, R3 and R4, which may be identical or different substituting groups, can be for example hydrogen atoms, alkyl chains which may comprise from 1 to 30 carbon atoms and especially from 1 to 16 carbon atoms, aryl chains such as benzyl, cycles, like for example cyclohexane, cyclooctane, or polycycles, like for example naphthalene, a polymer or any moiety having a chemical function with specific binding properties. If R1, R2, R3 and R4 are alkyl chains, some of these chains may also be branched on one ore several carbon atom(s) of said alkyl chains. Further, the alkyl chain may be substituted, for example by halogen atoms on one or several carbon atom(s) of said alkyl chain.

DISCLOSURE OF THE INVENTION

The present invention is distinct from prior art by the fact that the composition of the eluting solution allows to release the [18F] activity from the anion exchange resin or phase, so that the recovered solution is reactive and immediately usable for the labeling reactions without a further evaporation step.

The term "anion-exchange resin or phase" means any resin or chromatography phase on which sufficiently strong interactions between the exchange phase and the positively charged species such as covalent bonding, physisorption, chemisorption and/or electrostatic interactions allow the positively charged species on which the anion exchange occurs, such as ammonium, phosphonium or sulfonium species, to remain attracted during the whole extraction process. The term anion-exchange phase should also namely include both strong anion-exchanger and reversed or normal phase behaving as a weak anion exchanger (for example NH2-silica, DEAE-cellulose, etc.).

According to the invention, the eluting medium is a low water content, preferably <3% water, organic solution containing at least the following components: a first compound (A) which is a tertiary alcohol-function bearing molecule and a second compound (B) which is a phase transfer agent suitable for radiolabeling and which is necessary for the anion exchange process. The elution process is made possible by the combined effects of the phase transfer agent, which brings anions that can exchange with the fluoride trapped on the anion-exchange phase, and of the tertiary alcohol functions brought by first compound (A), which enhances the solubility of the ions, including the [18F] fluoride, in the organic medium. In this process, the [18F] activity remains in solution at all times, contrary to the prior art where it is recovered in a "dry form" on the surface of a reactor, as a result of the evaporation step. In addition, the presence of compound (A) makes the reaction less sensitive to the presence of water.

In this context, it has been shown by CHI, D. Y. et al [*A New Class of SN2 Reactions Catalyzed by Protic Solvents: Facile Fluorination for Isotopic Labeling of Diagnostic Molecules*, J. Am. Chem. Soc., Vol. 128, 50 (2006) pp. 16394-16397; WO-A-2006/065038] that the addition of some tertiary alcohols to the reaction mixtures subsequently to elution, usually composed of acetonitrile with the relevant precursor, does not impact unfavorably on the subsequent nucleophilic substitution reaction ("SN2" reactions).

According to the present invention, said elution process is performed by passing the eluting solution through a solid phase extraction column containing an anion-exchange phase. The [18F] fluoride is released from the phase in the eluting medium as specified above and is immediately usable for efficient radiolabeling.

In some embodiments of the present invention, prior to the elution process, the column is rinsed with an organic solvent that allows the elimination of the residual water that may be undesirable for a subsequent chemical processing, whilst keeping the extracted anions trapped on the anion-exchange phase.

In some embodiments of the present invention, this organic solvent can be selected among acetonitrile (ACN), dimethylsulfoxide (DMSO), dimethylacetamide, dimethylformamide (DMF), tetrahydrofuran (THF), diethylether, dioxane, ethyl acetate, acetone, isobutyronitrile, benzonitrile, pyridine, diethylcarbonate, sulfolane, hexamethylphosphotriamide (HMPA/HMPT), etc. or a mix of these solvents.

In some embodiments of the present invention, a non-polar organic solvent, such as an hydrocarbon or an alkane, is passed through the column to eliminate most of the remaining water, whilst keeping the extracted anions trapped on the anion-exchange phase.

In some preferred embodiments of the present invention, the non-polar organic solvent is selected from the group consisting of pentane, hexane, heptane, octane, nonane, decane and cyclohexane.

In some embodiments of the present invention, prior to the elution process, a drying step comprising a flush of gas such as air, nitrogen or argon can be used to purge the column and eliminate most of the remaining solvent.

In some embodiments of the invention this drying step is assisted by heating up the anion-exchange phase directly or indirectly by the flushing gas.

More specifically, according to the invention, the eluting medium is a low water content (<3%) organic solution of the first compound (A) bearing one or some tertiary alcohol or phenol functions, the second compound (B) that is said phase transfer agent suitable for radiolabeling and necessary for the anion exchange. All these compounds are selected in such a way that they have no unfavorable impact on the yield of the subsequent labeling reaction. Moreover, even with the presence of up to 3% of water, efficient labeling is possible due to the presence of the tertiary alcohol or phenol functions brought by compound (A).

In some embodiments of the invention, the solvent used to elute the anion-exchange phase is first compound (A).

In some embodiments of the invention, the solvent used to elute the anion-exchange phase is second compound (B).

In some embodiments of the invention, the organic solvent used to elute the anion-exchange phase is preferably selected from the group consisting of acetonitrile (ACN), dimethylsulfoxide (DMSO), dimethylacetamide, dimethylformamide (DMF), tetrahydrofuran (THF), diethylether, dioxane, ethyl acetate, acetone, isobutyronitrile, benzonitrile, pyridine, diethylcarbonate, sulfolane, hexamethylphosphotriamide (HMPA/HMPT), etc. and a mix of these solvents.

In some embodiments of the present invention, the eluting medium is heated up to enhance the elution efficiency.

In some embodiments of the present invention, the precursor for the labeling reaction is contained in the eluting medium.

In some embodiment of the invention, the eluted medium is diluted in a solvent suitable for the labeling step such as acetonitrile (ACN), dimethylsulfoxide (DMSO), dimethylformamide (DMF), tetrahydrofuran (THF), dioxane, ethyl acetate, sulfolane, hexamethyl-phosphotriamide (HMPA/HMPT), etc. and a mix of these solvents.

In some embodiments of the invention, the functionality brought by compound A and compound B can be on the same molecule, this molecule being used in the eluting medium. Such a compound can be for example quaternized 3-Hexyne-2,5-diol-2,5-di-3-pyridinyl, quaternized 2-Nonyn-4-ol-8-methoxy-4,8-dimethyl-1-[2-(3-pyridinyl)-1-piperidinyl], etc.

In some embodiments of the present invention, the first compound (A) used for the elution process is preferably selected from the group consisting of tertiary alcohols, diols and polyols with 1 to 20 tertiary alcohol functions such as for example t-butanol, t-amyl alcohol, 2,3-dimethyl-2-butanol and 2-(trifluoromethyl)-2-propanol, 2,8 dimethyl-decanediol, 2,8-dimethyl-3-Octyne-2,5-diol, 1,1'-(1,2-ethynediyl)bis-cyclohexanol, 1,1'-(1,2-ethynediyl)bis-cyclopentanol, 2,5-dimethyl-3-Hexene-2,5-diol.

In some embodiments of the present invention, the first compound (A) used for the elution process is preferably selected from the group consisting of phenols, with 1 to 20 phenol functions.

The second compound (B) can be selected from the group of metal cation salt complexes. The complexing agent ensures the ability of the organic solvent to dissolve the salt. The complexing agent itself can even behave as the second compound (B).

The metal salt cation is preferably selected from the alkali group consisting of lithium, sodium, potassium, rubidium, and cesium, from the alkaline earth metal group consisting of magnesium, calcium, strontium, and barium. The cation could also be an ammonium ($NH_4+$). The salt is preferably selected from the group consisting of halogenides (F, Cl, Br, I), hydroxide, carbonates, phosphates, sulfates, carboxylates, acetate, mesylate, alcoholates and perchlorate.

The complexing agent, suitable for the subsequent chemistry, can be comprised in the group of cryptands, including "kryptofix", such as 1,4,10-Trioxa-7,13-diaza-cyclopentadecane, 4,7,13,16,21,24-Hexaoxa-1,10-diazabicyclo[8.8.8]hexacosane, 4,7,13,16,21-Pentaoxa-1,10-diazabicyclo[8.8.5]tricosane, 4,7,13,18-Tetraoxa-1,10-diazabicyclo[8.5.5]eicosane, 5,6-Benzo-4,7,13,16,21,24-hexaoxa-1,10-diazabicyclo[8.8.8]hexacos-5-ene; the group glymes including crown ethers such as for example 4'-Aminobenzo-15-crown-5, 4'-Aminobenzo-15-crown-5, 4'-Aminobenzo-15-crown-5 hydrochloride, 4'-Aminobenzo-18-crown-6, 4'-Aminodibenzo-18-crown-6, 2-Aminomethyl-15-crown-5, 2-Aminomethyl-15-crown-5, 2-Aminomethyl-18-crown-6, 4'-Amino-5'-nitrobenzo-15-crown-5, 4'-Amino-5'-nitrobenzo-15-crown-5, 1-Aza-12-crown-4, 1-Aza-15-crown-5, 1-Aza-15-crown-5, 1-Aza-18-crown-6, 1-Aza-18-crown-6, Benzo-12-crown-4, 5,6-Benzo-4,7,13,16,21,24-hexaoxa-1,10-diazabicyclo[8.8.8]hexacos-5-ene, 1-Benzyl-1-aza-12-crown-4, Bis[(benzo-15-crown-5)-15-ylmethyl] pimelate, 4'-Bromobenzo-15-crown-5, 4-tert-Butylbenzo-15-crown-5, 4-tert-Butylcyclohexano-15-crown-5, 4'-Carboxybenzo-15-crown-5, polyethylene glycols (PEG), polyethylene oxides (PEO);

In some embodiments of the invention, the organic solvent used to elute the anion-exchange phase is the complexing agent used to solubilize the metal salt.

The complexing agent for the metal salt complex can also be found in the group of calixarenes such as for example 4-tert-Butylcalix[4]arene, 4-tert-Butylcalix[4]arene, 4-tert-Butylcalix[4]arene, 4-tert-Butylcalix[5]arene, 4-tert-Butylcalix[6]arene, 4-tert-Butylcalix[6]arene, 4-tert-Butylcalix[6]arene, 4-tert-Butylcalix[8]arene, 4-tert-Butylcalix[8]arene, 4-tert-Butylcalix[4]arene-tetraacetic acid tetraethyl ester, 4-tert-Butylcalix[4]arenetetraacetic acid tetraethyl ester, 4-tert-Butylcalix[4]arene-tetraacetic acid triethyl ester, Calix [4]arene, Calix[6]arene, Calix[8]arene, 4-(Chloromethyl) calix[4]arene, 4-Isopropylcalix[4]arene, C-Methylcalix[4] resorcinarene, C-Methylcalix[4]resorcinarene, meso-Octamethylcalix(4)pyrrole, 4-Sulfocalix[4]arene, 4-Sulfocalix[4]arene sodium salt, C-Undecylcalix[4]resorcinarene monohydrate, C-Undecylcalix[4]resorcinarene monohydrate.

The second compound (B) can be selected in the group of ammonium salts and more preferably the quaternary ammonium salts as shown in FIG. 1A. In this case, the role of the phase transfer agent and the salt are fulfilled by this ammonium salt.

The second compound (B) can be selected in the group of phosphonium salts and more preferably the quaternary phosphonium salts as shown in FIG. 1B. In this case, the role of the phase transfer agent and the salt are fulfilled by this phosphonium salt.

The second compound (B) can be selected in the group of ionic liquids including 1-Ethyl-3-methylimidazolium bromide, 1-Ethyl-3-methylimidazolium hexafluorophosphate, 1-Ethyl-3-methylimidazolium hexafluoroantimonate, 1-Ethyl-3-methylimidazolium tetrafluoroborate, 1-Ethyl-3-methylimidazolium trifluoromethanesulfonate, 1-Ethyl-3-methylimidazolium methanesulfate, 1-Ethyl-3-methylimidazolium tosylate, 1-Ethyl-3-methylimidazolium bis[salicylato(2-)]-borate, 1-Ethyl-3-methylimidazolium cobalt tetracarbonyl, 1-Butyl-3-methylimidazolium chloride (FutureChem Co LTD).

The eluted organic solution containing the [18F] fluoride can be used for the synthesis of a PET radiotracer. The [18F] fluoride is then reactive for nucleophilic substitution reactions.

In some embodiments of the present invention, the substitution reaction is directly performed on the said anion-exchange phase used for the recovery of the [18F] fluoride ions wetted by the eluting organic solution containing said first compound (A) and second compound (B) and containing a suitable precursor.

About the Water Content

It was disclosed in N. J. OSBORN et al. (WO-A-2006/054098) that some water content is mandatory to get high and reproducible labeling (nucleophilic substitution) yield. Indeed, amount of 0.1% to 0.7% water in the labeling medium is necessary. Moreover, the lack of water causes the yield to dramatically drop from 90% to 40%. In the present invention, the use of tertiary alcohol or phenol containing compounds in the elution medium advantageously improves the tolerance of the subsequent labeling reaction to both lack or excess of water ranging from 0% to 3%.

DESCRIPTION OF A PREFERRED EMBODIMENT OF THE INVENTION

Examples

1. Improved Tolerance of Nucleophilic Substitution to the Presence of Water

About 10 mCi was trapped on a QMA cartridge, (preconditioned with K2CO3, rinsed and dried).

The cartridge was quantitatively eluted with ~400 µL of a solution of Kryptofix in 50/50% water acetonitrile.

An evaporation was performed at ~120° C. to dryness in a V-vial.

The drying was completed by two small additions of acetonitrile followed each by a complete evaporation. Then 20 mgr of mannose triflate dissolved in 400 µL acetonitrile (dried on molecular sieve) was added. 400 µL of t-BuOH was added, and 40 µL of water was purposely added.

A heating for 15 minutes at 100° C. was performed.

The reaction was interrupted by addition of 2 ml of water.

A 40% yield on TLC (RF of the labeled tetra-acetyl) was obtained.

This experiment shows that the nucleophilic substitution reaction in a t-BuOH+ACN solution remains possible, although 5% water is present.

2. Improved Tolerance of Nucleophilic Substitution to the Presence of Water

About 10 mCi was trapped on a QMA cartridge, (preconditioned with K2CO3, rinsed and dried).

The cartridge was quantitatively eluted with ~400 µL of a solution of Kryptofix in 50/50% water-acetonitrile.

An evaporation was performed at ~120° C. to dryness in a V-vial.

The drying was completed by small additional acetonitrile evaporations.

Then 20 mg of mannose triflate dissolved in 400 µL acetonitrile (dried on molecular sieve) was added. 400 µL of t-amyl-alcohol was added, and 40 µL of water was purposely added.

A heating was performed for 15 minutes at 100° C. The reaction was interrupted by addition of 2 ml of water.

A ~36% yield on TLC (RF of the labeled tetra-acetyl) was obtained.

This experiment shows that the nucleophilic substitution reaction in a t-amyl-alcohol+ACN solution remains possible, although 5% water is present.

3. Improved Tolerance of Nucleophilic Substitution to the Presence of Water

To 200 µL of water containing 5.5 mCi of [18F] were added 690 µL of a solution of Kryptofix in 50/50% water-acetonitrile.

An evaporation was performed at ~120° C. to dryness in a V-vial.

The drying was completed by small additional acetonitrile evaporations.

Then 15 mg of mannose triflate dissolved in 500 µL DMSO and 500 µL of t-amyl-alcohol was added, and 10 µL of water (1%) was purposely added.

A heating was performed for 5 minutes at 100° C.

A ~90% yield on TLC(RF of the labeled tetra-acetyl) was obtained.

This experiment shows that high yield nucleophilic substitution reaction in a ACN+t-amyl-alcohol solution can be achieved, although 1% water is present.

4. Effect of the Alcohol on a QMA Elution Process

About ~1.25 mCi was trapped on a QMA cartridge (preconditioned with K2CO3, rinsed and dried).

The cartridge was rinsed with 2 mL of acetonitrile, then dried with nitrogen flow for 2 minutes.

An elution was performed with a solution of TBA-hydroxide dissolved in a 1 M solution of t-amyl-alcohol in acetonitrile. 95.5% of the activity was eluted in the first 900 µL of elutant.

5. QMA Elution Followed by Labeling in the Eluted Solution, without Evaporation

About ~10 mCi was trapped on a QMA cartridge (preconditioned with K2CO3, rinsed and dried).

The cartridge was rinsed with 2 mL of acetonitrile, then dried with nitrogen flow for 2 minutes.

An elution was performed with a solution of TBA-hydroxide dissolved in a 50/50% mixture t-butanol-acetonitrile. 50% of the activity was eluted in the first 500 µL of elutant.

Mannose-triflate was added in this mixture and heated the mixture at 100° C. for 5 minutes. A TLC-yield of 90% was measured.

This experiment shows that an elution mixture can be formulated that allows a fair elution and a fair substitution reaction yield.

6. QMA Elution Followed by Labeling in the Eluted Solution, without Evaporation About 1.5 mCi was trapped on a QMA cartridge, (preconditioned with K2CO3, rinsed and dried). The cartridge was rinsed with 2 mL of acetonitrile, then dried with nitrogen flow for 2 minutes.

An elution was performed with a solution containing 11 mg TEA-hydroxide dissolved in 1 mL of DMSO. 60-70% of the activity was eluted in the first 300 µL.

Mannose-triflate was added in this mixture and heated the mixture at 100° C. for 5 minutes. A TLC-yield of 25% was measured.

This experiment shows that a formulation including the mentioned ingredients allows a fair elution yield while the labeling reaction has not been completely inhibited, and remains possible.

7. QMA Elution Followed by Improved Labeling in the Eluted Solution, without Evaporation About 15 mCi was trapped on a QMA cartridge, (preconditioned with K2CO3, rinsed and dried).

The cartridge was rinsed with 2 mL of acetonitrile, then dried with nitrogen flow for 2 minutes.

An elution was performed with a solution containing 20 mg TBA-hydroxide dissolved in 1 mL of 50/50 ACN/t-amyl-alcohol. 87% of the activity was eluted.

25 mg mannose-triflate dissolved in 700 µL of 50/50% ACN/t-amyl-alcohol was added and the mixture heated at 100° C. for 5 minutes. A TLC-yield of 88% was measured.

8. QMA Elution Followed by Improved Labeling in the Eluted Solution, without Evaporation About 21 mCi was trapped on a QMA cartridge, (preconditioned with K2CO3, rinsed and dried).

The cartridge was rinsed with 2 mL of acetonitrile.

An elution was performed with a solution containing 20 mg TBA-hydroxide dissolved in 1 mL of 50/50% ACN/t-amyl-alcohol. 89% of the activity was eluted.

17 mg mannose-triflate dissolved in 1 mL of 50/50 ACN/t-amyl-alcohol was added and the mixture heated at 100° C. for 5 minutes. A TLC-yield of 88% was measured.

9. QMA Elution Followed by Improved Labeling in the Eluted Solution, without Evaporation About 25 mCi was trapped on a QMA cartridge, (preconditioned with K2CO3, rinsed and dried).

The cartridge was rinsed with 2 mL of acetonitrile.

An elution was performed with a solution containing 27 mg TBA-hydroxide dissolved in 1 mL of 50/50% ACN/t-amyl-alcohol. 94% of the activity was eluted.

20 mg mannose-triflate dissolved in 1 mL of 50/50% ACN/t-amyl-alcohol was added and the mixture heated at 100° C. for 5 minutes. A TLC-yield of 76% was measured.

This experiment showed that a formulation can be progressively optimized that combines a fair elution yield with a fair labeling yield.

10. QMA Elution Followed by Improved Labeling in the Eluted Solution, without Evaporation About 712 µCi was trapped on a QMA cartridge, (preconditioned with K2CO3, rinsed and dried).

The cartridge was rinsed with 2 mL of acetonitrile.

An elution was performed with a solution containing TBA-hydroxide dissolved in 1 mL of 1 M 2,6-dimethyl-hexanediol. 85.5% of the activity was eluted in the first 300 µl of the eluting solution.

Terms and Acronyms

QMA cartridge: solid phase extraction cartridge containing anion-exchange phase such as or similar to quaternary ammonium species
TBA: tetrabutyl ammonium
TEA: tetraethyl ammonium
DMSO: dimethylsulfoxide
ACN: acetonitrile
t-BuOH: tert-butanol
TCL: thin layer chromatography
RF: retention factor

The invention claimed is:

1. A method to extract out of an aqueous solution, concentrate and/or reformulate [18F] fluorides without any evaporation step, said method comprising the following steps of:
    passing said aqueous [18F] fluoride solution through a solid phase extraction column containing an anion-exchange phase so that said [18F] fluorides are trapped thereon;
    eluting said [18F] fluorides with an eluting solution so that to release said [18F] fluorides from said anion-exchange phase under the form of a solution which is reactive and immediately usable for a labeling reaction;
    wherein the eluting solution is an organic solution having a water content lower than 3% and containing at least:
        a first compound which is a tertiary alcohol-function bearing molecule,
        a second compound which is a phase transfer agent suitable for radiolabeling and which is necessary to the anion-exchange process.

2. Method according to claim 1, wherein, prior to the elution step, the column is rinsed with an organic solvent so that to eliminate the residual water that may be undesirable for a subsequent chemical processing, whilst keeping the extracted anions trapped on the anion-exchange phase.

3. Method according to claim 2, wherein said organic solvent is selected from the group consisting of acetonitrile (ACN), dimethylsulfoxide (DMSO), dimethylacetamide, dimethylformamide (DMF), tetrahydrofuran (THF), diethyl-ether, dioxane, ethyl acetate, acetone, isobutyronitrile, benzonitrile, pyridine, diethylcarbonate, sulfolane, hexamethylphosphotriamide (HMPA/HMPT) and any mix of these solvents.

4. Method according to claim 2, wherein a non-polar organic solvent, such as an hydrocarbon or alkane, is passed through the column to eliminate most of the remaining water, whilst keeping the extracted anions trapped on the anion-exchange phase.

5. Method according to claim 4, wherein said non-polar organic solvent is selected from the group consisting of pentane, hexane, heptane, octane, nonane, decane and cyclohexane.

6. Method according to claim 1, prior to the elution step, further comprising a drying step in which a flush of gas such as air, nitrogen or argon is used to purge the column and eliminate most of the remaining solvent.

7. Method according to claim 6, wherein the drying step is assisted by heating up the anion-exchange phase.

8. Method according to claim 1, wherein the first compound (A) bears one or more tertiary alcohol functions.

9. Method according to claim 1, wherein said eluting solution contains the first compound as a solvent.

10. Method according to claim 1, wherein said eluting solution contains the second compound as a solvent.

11. Method according to claim 1, wherein the eluting solution of the anion exchange phase comprises an organic solvent selected from the group consisting of acetonitrile (ACN), dimethylsulfoxide (DMSO), dimethylacetamide, dimethylformamide (DMF), tetrahydrofuran (THF), diethylether, dioxane, ethyl acetate, acetone, isobutyronitrile, benzonitrile, pyridine, diethylcarbonate, sulfolane, hexamethylphosphotriamide (HMPA/HMPT) and any mix of these solvents.

12. Method according to claim 1, wherein the eluting solution is heated up to enhance the elution efficiency.

13. Method according to claim 1, wherein a precursor for the labeling reaction is contained in the eluting solution.

14. Method according to claim 1, wherein the eluted solution is diluted in a solvent suitable for the labeling step and selected from the group consisting of acetonitrile (ACN), dimethylsulfoxide (DMSO), dimethylformamide (DMF), tetrahydrofuran (THF), dioxane, ethyl acetate, sulfolane, hexamethylphosphotriamide (HMPA/HMPT) and any mix of these solvents.

15. Method according to claim 1, wherein the functionalities brought by the first compound and the second compound are on the same molecule, the same molecule being used in the eluting solution.

16. Method according to claim 15, wherein said same molecule is selected from the group consisting of quaternized 3-Hexyne-2,5-diol-2,5-di-3-pyridinyl and quaternized 2-Nonyn-4-ol-8-methoxy-4,8-dimethyl-1-[2-(3-pyridinyl)-1-piperidinyl].

17. Method according to claim 1, wherein the first compound used for the elution step is selected from the group consisting of tertiary alcohols, diols and polyols with 1 to 20 tertiary alcohol functions such as t-butanol, t-amyl alcohol, 2,3-dimethyl-2-butanol and 2-(trifluoromethyl)-2-propanol, 2,8 dimethyl-decanediol, 2,8-dimethyl-3-Octyne-2,5-diol, 1,1'-(1,2-ethynediyl)bis-cyclohexanol, 1,1'-(1,2-ethynediyl)bis-cyclopentanol, 2,5-dimethyl-3-Hexene-2,5-diol.

18. Method according to claim 1, wherein the second compound is a metal salt cation complex, so that the functional role of the transfer agent and a salt function are fulfilled by this metal salt complex.

19. Method according to claim 18, wherein said metal salt cation is selected from the group consisting of the alkali group, preferably lithium, sodium, potassium, rubidium and cesium, the alkaline earth metal group, preferably magnesium, calcium, strontium and barium, and ammonium ($NH_4+$).

20. Method according to claim 18, wherein the salt is selected from the group of halogenides, consisting of fluor, chlor, brome and iode, hydroxide, carbonates, phosphates, sulfates, carboxylates, acetate, mesylate, alcoholates and perchlorate.

21. Method according to claim 18, wherein the complexing agent, suitable for the subsequent chemistry, is selected from the group consisting of cryptands, including kryptofixs such as 1,4,10-Trioxa-7,13-diaza-cyclopentadecane, 4,7,13,16, 21,24-Hexaoxa-1,10-diazabicyclo [8.8.8]hexacosane, 4,7,13,16,21-Pentaoxa-1,10-diazabicyclo[8.8.5]tricosane, 4,7,13,18-Tetraoxa-1,10-diazabicyclo [8.5.5]eicosane, 5,6-Benzo-4,7,13,16,21,24-hexaoxa-1,10-diazabicyclo[8.8.8] hexacos-5-ene; the group glymes including crown ethers such as for example 4'-Aminobenzo-15-crown-5, 4'-Aminobenzo-15-crown-5, 4'-Aminobenzo-15-crown-5 hydrochloride, 4'-Aminobenzo-18-crown-6,4'-Aminodibenzo-18-crown-6, 2-Aminomethyl-15-crown-5,2-Aminomethyl-15-crown-5, 2-Aminomethyl-18-crown-6,4'-Amino-5'-nitrobenzo-15-crown-5,4'-Amino-5'-nitrobenzo-15-crown-5,1-Aza-12-crown-4, 1-Aza-15-crown-5,1-Aza-15-crown-5,1-Aza-18-crown-6,1-Aza-18-crown-6, Benzo-12-crown-4,5,6-Benzo-4,7,13,16,21,24-hexaoxa-1,10-diazabicyclo [8.8.8]hexacos-5-ene, 1-Benzyl-1-aza-12-crown-4, Bis[(benzo-15-crown-5)-15-ylmethyl] pimelate, 4'-Bromobenzo-15-crown-5,4-tert-Butylbenzo-15-crown-5,4-tert-Butylcyclohexano-15-crown-5,4'-Carboxybenzo-15-crown-5, polyethylene glycols (PEG), polyethylene oxides (PEO).

22. Method according to claim 18, wherein the eluting solution of the anion exchange phase comprises, as an organic solvent, the complexing agent used to solubilize the metal salt.

23. Method according to claim 18, wherein the complexing agent for the metal salt complex is selected from the group of calixarenes such as for example 4-tert-Butylcalix[4]arene, 4-tert-Butylcalix[4]arene, 4-tert-Butylcalix[4] arene, 4-tert-Butylcalix[5] arene, 4-tert-Butylcalix[6] arene, 4-tert-Butylcalix[6]arene, 4-tert-Butylcalix[6] arene, 4-tert-Butylcalix [8] arene, 4-tert-Butylcalix[8] arene, 4-tert-Butylcalix[4] arene-tetraacetic acid tetraethyl ester, 4-tert-Butylcalix[4] arenetetraacetic acid tetraethyl ester, 4-tert-Butylcalix[4] arene-tetraacetic acid triethyl ester, Calix[4]arene, Calix[6] arene, Calix[8]arene, 4-(Chloromethyl)calix[4] arene, 4-Isopropylcalix[4] arene, C-Methylcalix[4]resorcinarene, C-Methylcalix[4]resorcinarene, meso-Octamethylcalix(4) pyrrole, 4-Sulfocalix[4] arene, 4-Sulfocalix[4]arene sodium salt, C-Undecylcalix[4]resorcinarene monohydrate, C-Undecylcalix[4]resorcinarene monohydrate.

24. Method according to claim 1, wherein the second compound comprising quaternary ammonium salts.

25. Method according to claim 1, wherein the second compound comprising quaternary phosphonium salt.

26. Method according to claim 1, wherein the second compound (B) is selected from the group consisting of ionic liquids including 1-Ethyl-3-methylimidazolium bromide, 1-Ethyl-3-methylimidazolium hexafluorophosphate, 1-Ethyl-3-methylimidazolium hexafluoroantimonate, 1-Ethyl-3-methylimidazolium tetrafluoroborate, 1-Ethyl-3-methylimidazolium trifluoromethanesulfonate, 1-Ethyl-3-methylimidazolium methanesulfate, 1-Ethyl-3-methylimidazolium tosylate, 1-Ethyl-3-methylimidazolium bis[salicylato (2-)]-borate, 1-Ethyl-3-methylimidazolium cobalt tetracarbonyl, 1-Butyl-3-methylimidazolium chloride (FutureChem Co LTD), the respective functional roles of the phase transfer agent and the salt being fulfilled by said ionic liquid.

27. Method according to claim 1, wherein the eluted solution, i.e. the organic solution containing [18F] fluoride after elution, is used for the synthesis of a PET radiotracer so that [18F] fluoride is reactive for nucleophilic substitution.

28. Method according to claim 27, wherein the substitution reaction is directly performed on the said anion exchange phase used for the recovery of the [18F] fluoride ions wetted by the eluting organic solution containing said first compound and second compound and containing a suitable precursor.

* * * * *